US009766168B2

(12) United States Patent
Meegan et al.

(10) Patent No.: US 9,766,168 B2
(45) Date of Patent: Sep. 19, 2017

(54) ACOUSTIC PARTICULATE CONCENTRATION METHODS AND SYSTEM

(71) Applicant: Applied Research Associates, Inc., Albuquerque, NM (US)

(72) Inventors: G. Douglas Meegan, Littleton, CO (US); Brian Zadler, Golden, CO (US); Jason R. Gallia, Houston, TX (US); Paul Waters, Littleton, CO (US)

(73) Assignee: Applied Research Associates, Inc., Albuquerque, NM (US)

( * ) Notice: Subject to any disclaimer, the term of this patent is extended or adjusted under 35 U.S.C. 154(b) by 237 days.

(21) Appl. No.: 14/521,156

(22) Filed: Oct. 22, 2014

(65) Prior Publication Data

US 2015/0107335 A1 Apr. 23, 2015

Related U.S. Application Data

(60) Provisional application No. 61/894,679, filed on Oct. 23, 2013.

(51) Int. Cl.
*G01N 1/10* (2006.01)
*G01N 1/40* (2006.01)
(Continued)

(52) U.S. Cl.
CPC ............ *G01N 1/4077* (2013.01); *G01N 1/10* (2013.01); *G01N 1/2202* (2013.01); *G01N 15/0255* (2013.01); *G01N 2001/4094* (2013.01)

(58) Field of Classification Search
CPC .... G01N 15/0255; G01N 1/10; G01N 1/2202; G01N 1/4077; G01N 2001/4094;
(Continued)

(56) References Cited

U.S. PATENT DOCUMENTS 4,747,920 A 5/1988 Muralidhara et al.
5,626,767 A 5/1997 Trampler et al.
(Continued)

OTHER PUBLICATIONS

Patent Cooperation Treaty, International Preliminary Report on Patentability, dated May 6, 2016.
(Continued)

*Primary Examiner* — Peter Macchiarolo
*Assistant Examiner* — Alexander Mercado
(74) *Attorney, Agent, or Firm* — Dinsmore & Shohl LLP; Monika L'Orsa Jaensson, Esq.

(57) ABSTRACT

A process is disclosed for using multiple acoustic resonators to sample fluids (gas or liquids), capture particulate (or aerosols) entrained in the fluid, and deliver a concentrated sample of particulate. The acoustic concentrator demonstrates many improvements over prior art that includes improved concentration of particulate below 3 micron, adjustability of the level of concentration, ability to function over a wide range of humidity and temperature, and reduced overall power consumption. For example, when installed on the inlet of an aerosol detection system, the acoustic concentrator has been shown to increase sensitivity that may lead to earlier detection of bioaerosol agents.

8 Claims, 16 Drawing Sheets
(2 of 16 Drawing Sheet(s) Filed in Color)

(51) Int. Cl.
*G01N 15/02* (2006.01)
*G01N 1/22* (2006.01)

(58) Field of Classification Search
CPC .... B01D 43/00; B01D 21/283; B01D 49/006;
B01D 61/56; B01J 19/10; G10K 11/04;
H03H 3/02; H03H 3/04; H03H 9/173;
H03H 9/585; H03H 9/587; H04R 1/1016;
H04R 1/1058
See application file for complete search history.

(56) References Cited

U.S. PATENT DOCUMENTS

| | | | |
|---|---|---|---|
| 6,068,079 A | 5/2000 | Hamery et al. | |
| 6,070,693 A | 6/2000 | Hamery | |
| 6,148,821 A | 11/2000 | Falco | |
| 6,384,697 B1 | 5/2002 | Ruby | |
| 6,797,158 B2 * | 9/2004 | Feke | B01D 21/0012 210/106 |
| 2003/0015035 A1 | 1/2003 | Kuduchak et al. | |
| 2009/0158823 A1 * | 6/2009 | Kaduchak | G01N 15/1404 73/61.75 |
| 2011/0151577 A1 * | 6/2011 | Zhang | B01L 3/5082 436/175 |
| 2011/0176976 A1 * | 7/2011 | Ebi | G01N 35/04 422/547 |
| 2011/0192969 A1 | 8/2011 | Verentchikov | |
| 2012/0325727 A1 * | 12/2012 | Dionne | B03B 5/00 209/155 |
| 2015/0021238 A1 * | 1/2015 | Gandhi | B07B 1/06 209/235 |
| 2015/0079655 A1 * | 3/2015 | Laugharn, Jr. | B01D 43/00 435/173.7 |
| 2016/0059206 A1 * | 3/2016 | Chen | G10K 15/00 210/748.05 |

OTHER PUBLICATIONS

Patent Cooperation Treaty, International Search Report and the Written Opinion of the International Searching Authority, dated Feb. 27, 2015.

* cited by examiner

ACOUSTIC PARTICULATE CONCENTRATION METHODS AND SYSTEM

BACKGROUND OF THE INVENTION

The present invention regards an acoustic concentrator system and method for capturing particulates entrained in gaseous (e.g., aerosol) or liquid fluids, and delivering a concentrated sample or stream of the particulate. In some embodiments the system and method can further provide a continuous flow of concentrated particulate. By concentrating the particulate entrained in gaseous or liquid fluids, the system of the present invention can be used to more effectively and accurately sample fluids for particulates.

Prior art related to aerosol concentration relies on inertial methods of particle separation and concentration within, typically, an air stream. Specifically, when an air stream containing particulate undergoes acceleration, the relatively high inertia of the particulate (as compared to the surrounding air) causes relative motion between the air and particulate, allowing the particulate to be separated from the air. For example, a virtual slit impactor is a well-known aerosol concentrator that concentrates particulate by extracting a minor flow that contains more particulate through a narrow aperture or slit, while the major flow containing less particulate is drawn through a 90-degree turn in the housing (the inertia of the particulate makes it difficult to continue through the turn). However, high humidity (>90%) air can cause condensation and accumulation of particulate on internal surfaces (e.g., precisely machined knife edges for diverting major and minor air flows), which negatively impacts the concentration of particulate delivered by the system. Furthermore, the inertia methods are less effective as the size of the particulate decreases (e.g., below 3 microns).

In contrast to the prior art, the present invention uses a fundamentally different approach to particulate concentration, exploiting the physical interaction between a sound field and a particulate. In the system and method of the present invention, the sound field is used to force particulates entrained in a fluid towards storage locations near or within nodal and anti-nodal positions within an acoustic resonator. When the sound field is activated at a sufficiently high sound pressure level, the acoustic force overcomes other forces experienced by particulate, e.g., air flow and viscous drag. Particulates are thereby trapped in storage locations of the resonator. When the sound field is deactivated, the particulate is released from the storage locations and is delivered by the system of the present invention as a concentrated stream of particulate.

The present invention is thereby a novel improvement over prior art systems. As hereinafter discussed, the invention expands the application methods to include particulate concentration in fluids, improves concentration of particulates below 3 micron, provides a more compact system, allowing for adjustability of the level of concentration, functions over a wide range of humidity and temperature (as the system does not provide machined knife edges that may accumulate particulates in high humidity), and consumes less overall power than the prior art systems.

Useful applications of the system and method of the present invention include integration into the inlet of an aerosol detection system, whereby the present invention increases the sensitivity of the detection system by concentrating particulates within the sampled air, leading to earlier detection of aerosol agents. Other applications include improving the sensitivity of other biological, chemical, radionuclide, and explosives sensors, by delivering a more effective sample of particulates entrained in a fluid. Similarly, the system and methods of the present invention may be used to process powdered materials, such as in the manufacturing of pharmaceutical powders.

SUMMARY OF THE INVENTION

Device.

The acoustic concentrator system of the present invention includes one or more structure-filled acoustic resonators and means for applying a sound field within the resonators. The sound pressure level and the frequency of the applied sound field are selected to trap a desired particulate or aerosol within the resonator—specifically, the sound field tends to move the particle into an acoustic node/anti-node where it temporarily held in place as a result of the applied sound field. By removing or altering the sound field, trapped particulate can be released from near the structured material and expelled from the resonator. Further, the system includes means for drawing into the resonator an air or liquid sample from the environment, means for expelling excess air or liquid from the resonator, and means for periodically or continuously releasing from the resonator a concentrated stream of the particulate.

Method.

The acoustic concentrator method of the present invention removes and concentrates particulates entrained in a fluid using one or more structure-filled acoustic resonators, such as the system herein described. In one embodiment, the resonator is filled with a fiber material. In other embodiments, the resonator may be filled with other materials such as a mesh grid, granular material, or honeycomb structure. The method includes the steps of drawing into the resonator an air sample having particulate entrained therein and applying an acoustic field within the resonator to cause the particulate to be temporarily trapped within the structured network of the resonator. The acoustic field of the method of the present invention has sound pressure level and/or frequency selected to dislodge the particulate from the fluid and trap the particulate near the structures. The method of the present invention further includes the steps of expelling excess air from the resonator, and periodically or continuously releasing from the resonator a concentrated stream of the particulate in a fluid. In some embodiments this process is cycled in a sequence among a series of resonators, wherein at least one resonator is providing a concentrated release of particulate, to achieve a continuous-flow of concentrated particulate.

The method of the present invention may further comprise sensing or sampling the concentrated particulate within or released from the resonator. Devices suitable for use to accomplish such sensing/sampling include fluorescent aerosol detection systems and other biological, chemical, radionuclide, and explosives sensors. Specifically, one may position these sensors near the outlet of the acoustic concentrator device, or the sensor may be positioned to sense the contents within the acoustic resonator. A transparent acoustic resonator may also be constructed to permit optical detection of aerosols within the resonator itself.

FIGURES

The patent or application file contains at least one drawing executed in color (see FIG. 1). Copies of this patent or patent application publication with color drawing(s) will be provided by the Office upon request and payment of the necessary fee.

DETAILED DESCRIPTION

The present invention relates to novel methods and systems for capturing aerosols or particulates entrained in gaseous or liquid fluids using a high-amplitude sound field in a structure-filled resonator, to achieve particulate (including aerosol) concentration and deliver a concentrated sample or stream of the particulate.

System—

As shown in FIGS. 2, 5, 11 and 12, the acoustic concentrator system of the present invention includes one or more structure-filled acoustic resonators 1 and means 2 for applying and removing a sound field within the resonators. The sound pressure level and the frequency of the applied sound field are selected to trap a desired particulate or aerosol within the resonator; by removing or altering the sound field, trapped particulate can be released from the structure and expelled from the resonator. Further, the system includes means 3 for drawing into the resonator an air or liquid sample from the environment, means 4 for expelling air or liquid from the resonator. In some embodiments, the expulsion means 4 includes at least two additional output ports, one 14A for expelling excess fluid from the resonator, and a second 14B for periodically or continuously releasing or gathering from the resonator a concentrated stream of the particulate. In these embodiments the expulsion means 4 may further include a single fan or similar conveyance mechanism, or a plurality of conveyance mechanisms, one associated with each expulsion port.

Figure 12:
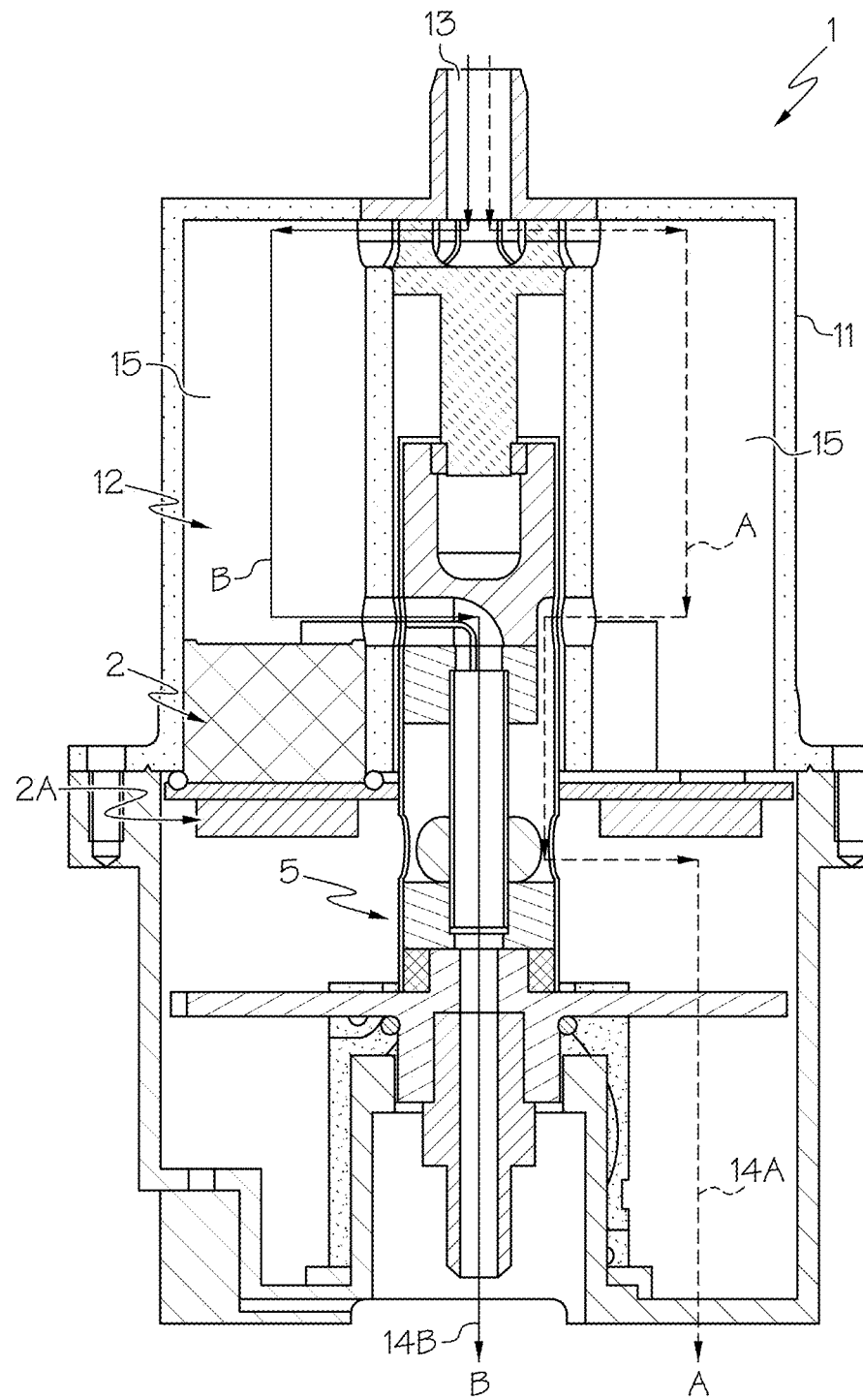
FIG. 12 depicts another embodiment of the resonator of the system of the present invention.

As shown in FIG. 12, the acoustic resonator 1 of the system of the present invention may have a housing 11 to define a chamber or cavity 12 generally cylindrical in shape, or have any other three-dimensional shape, such as parallelepiped to form the body of an acoustic resonator. In some embodiments the cylindrical cavity 12 may have a diameter of from about 1/10" up to about 24"; more typically 1/4" up to 2", in some embodiments the cavity has a diameter of from about 1/4" to about 1"; in some embodiments the diameter is 5/8". The resonator cavity may have a length of from about 1/4" to about 24"; in some embodiments this length may be between 1/4" and 2"; in other embodiments this length may be between 2" and 12". The length of the housing 11 may be adjusted so that the cavity resonance matches the natural frequency of the sound source, thereby achieving maximum efficiency and a resulting high sound pressure level. For example, in a simple one-dimensional resonator, resonance occurs at chamber lengths given by Length=½×N×(frequency of applied sound)/(speed of sound) where N=1, 2, 3, . . . . The resonator housing 11 may be constructed or molded out of any material, organic or inorganic, including metal, plastic, stone, and wood.

Figure 2:
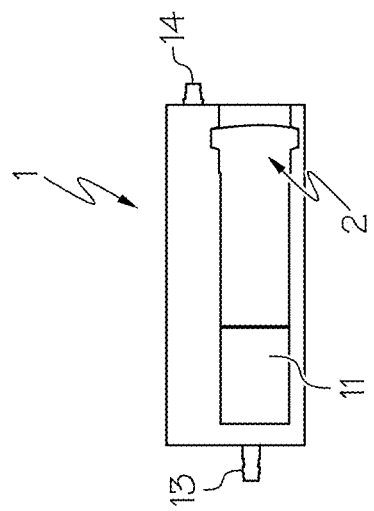
FIG. 2 is a depiction of a single-resonator embodiment of the system of the present invention.
Figure 2:
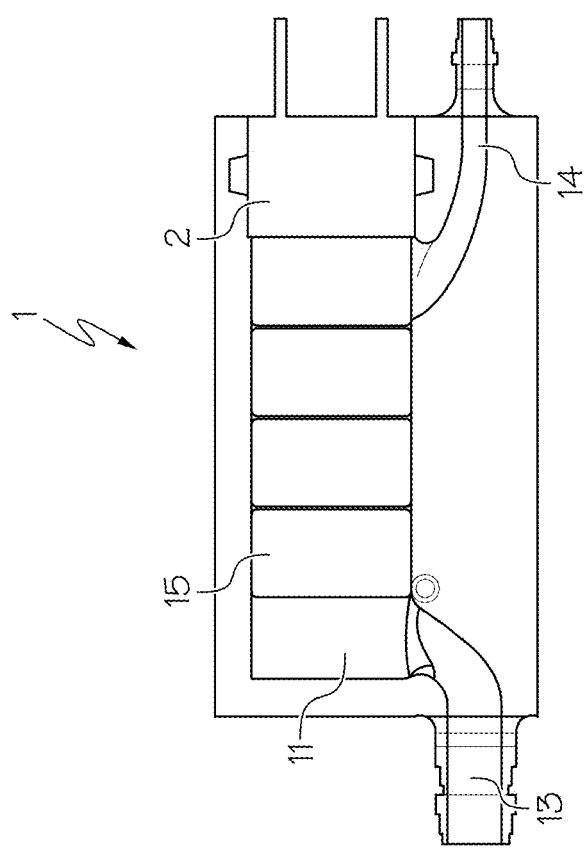
Figure 11:
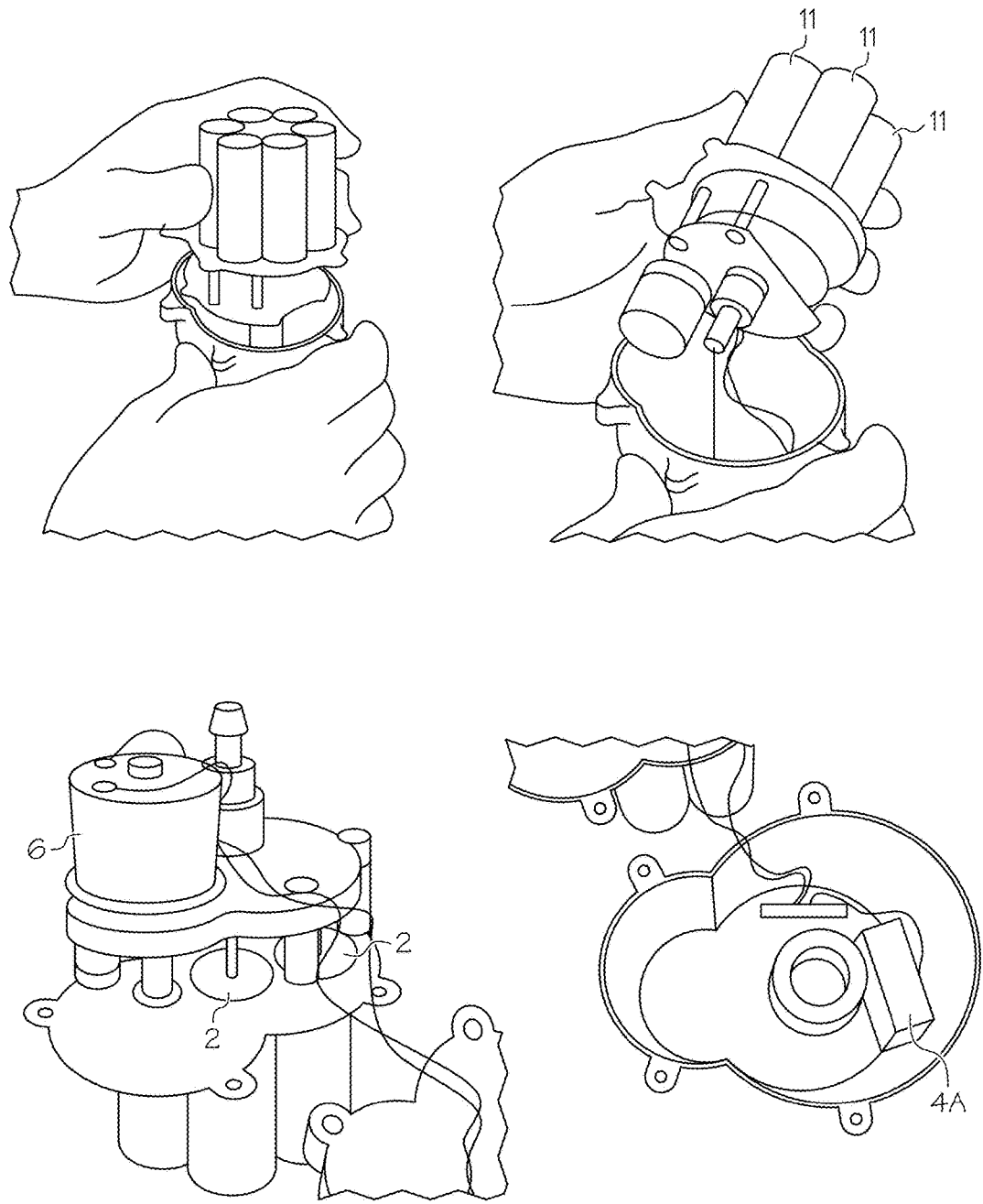
FIG. 11 depicts another embodiment of the system of the present invention, including multiple resonators.

As shown in FIGS. 11 and 12, the acoustic resonator housing 11 includes an inlet port 13 and an outlet port 14A for air to pass through the device. Preferably the inlet port 13 and the outlet port 14A are positioned on or near opposing ends of the housing 11, so that the air passes from the inlet port through a large percentage of the structure-filled resonator before exiting the resonator at the outlet port. In some embodiments (as shown in FIGS. 2 and 12) the inlet port 13 is an aperture at, or tube extending from, the top of the housing 11, and the outlet port 14 or 14A is an aperture at, or tube extending from, the bottom of the housing. Fluid is drawn through the inlet port 13 and the outlet port 14 by a fan 4A or other conveyance means.

As shown in FIGS. 2, 5, 11 and 12, the acoustic concentrator system of the present invention includes one or more structure-filled acoustic resonators 1 and means 2 for applying and removing a sound field within the resonators. The sound pressure level and the frequency of the applied sound field are selected to trap a desired particulate or aerosol within the resonator; by removing or altering the sound field, trapped particulate can be released from the structure and expelled from the resonator. Further, the system includes means 4A or 5 for drawing into the resonator an air or liquid sample from the environment and for expelling air or liquid from the resonator. In some embodiments, the expulsion means 4A or 5 includes at least two additional output ports, one 14A for expelling excess fluid from the resonator, and a second 14B for periodically or continuously releasing or gathering from the resonator a concentrated stream of the particulate. In these embodiments the expulsion means 4A or 5 may further include a single fan or similar conveyance mechanism, or a plurality of conveyance mechanisms, one associated with each expulsion port.

The inlet 13 and outlet port apertures or tubes 14, 14A or 14B may be about 1/8" diameter for the case of a 5/8" resonator, but they may vary in diameter depending on the size of the resonator cylinder. The diameter of the outlet should be small in order to effectively contain the sound field and maintain efficient resonance.

Figure 1:
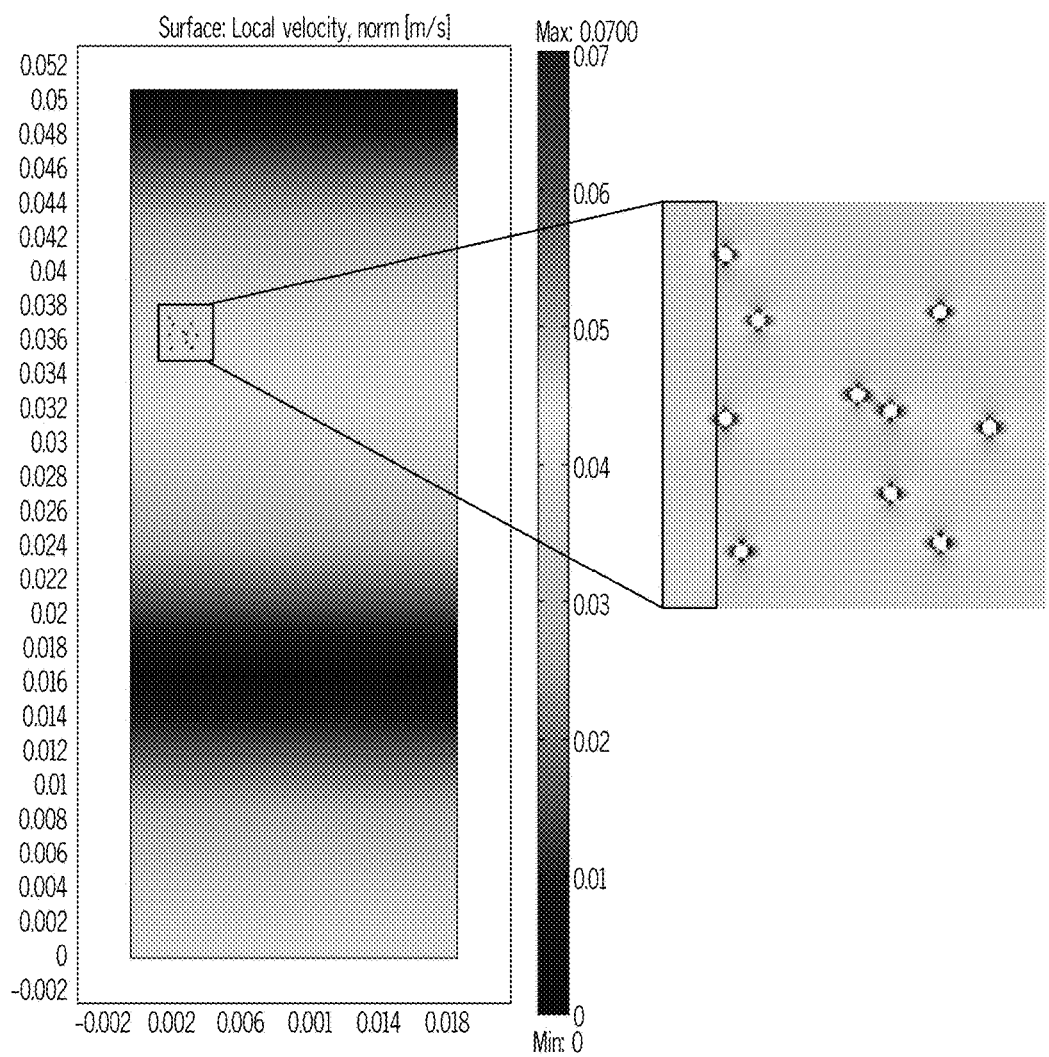
FIG. 1 is a numerical simulation of the number of acoustic storage locations within a fibrous resonator chamber.

By introducing a structured material 15 inside of the acoustic resonator 1, the density of acoustic storage locations (nodes and anti-nodes) for particulate matter is greatly increased near the surface of the structure due to the creation of a complex sound field that is rich in nodal structure. This effect is numerically simulated in FIG. 1, a cut view of a representative resonator cavity, with a standing wave field established through the application of sound from a sound source at one end, wherein the addition of a structured material serves to superimpose additional velocity nodes onto the bulk sound field. Notably, in this figure nodes appear along the length of the cylinder—at the top and about one-third up from the bottom, and smaller-sized nodes are near the surface of every structure. With this increased density of storage locations, the resonator of the present invention dramatically increases the quantity of particles that may be temporarily stored in the structure network while the sound field is activated.

Figure 1A:
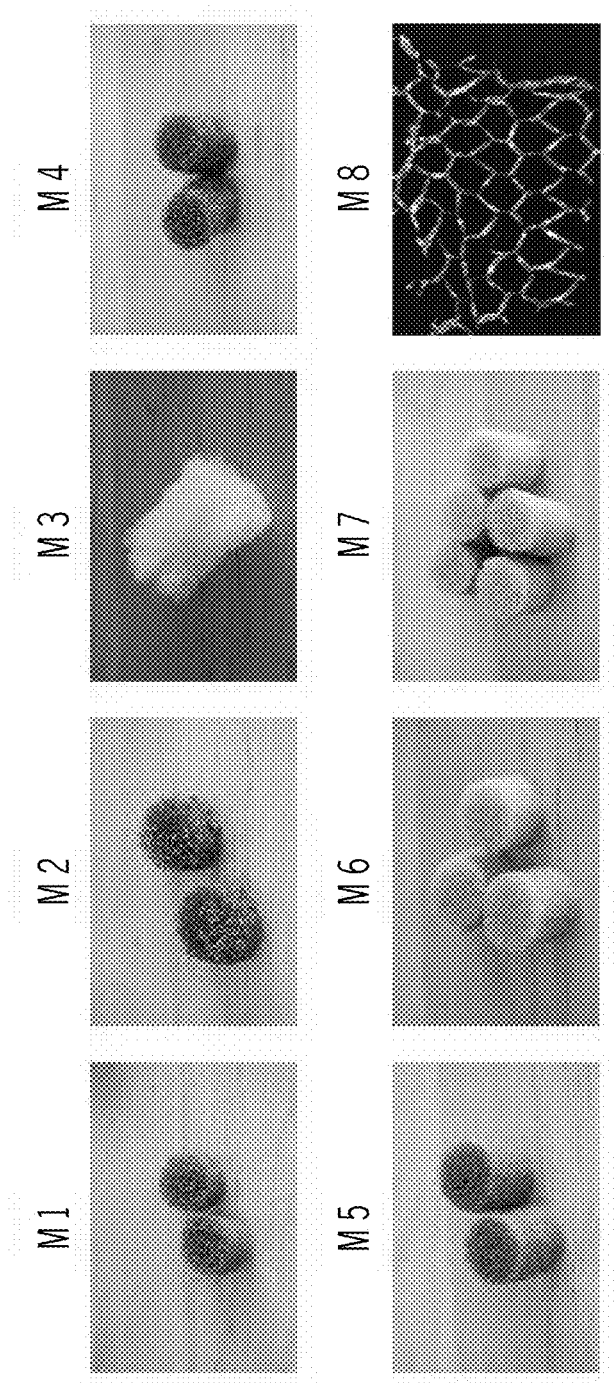
FIG. 1A is a depiction of various fibers suitable for use in the acoustic resonator of the present invention.

The particle storage and concentration capacity of the present invention can be observed whether the resonator chamber 12 is partially or entirely filled with structured material 15. The structured material need only be porous in nature with interconnected pore spaces. Examples include, but are not limited to, fibers, metallic fibers (including but not limited to aluminum fiber), meshes, open cell foams, nylon fibers and granular media. FIG. 1A shows structured materials suitable for use in the present invention, wherein M1 and M2 are nylon fiber mesh as is commonly used in household dishpan scrub pads, M3 is a loose fiber material as is commonly used in cushions or pillows, M4-M7 are various foams commonly used for padding in packaging items for shipping, and M8 is an aluminum mesh. While the bulk porosity of the materials affects what particle diameters can efficiently flow through without significant impaction losses, materials with porosities ranging from 5% to 99% can be utilized for particle concentration in the systems and methods of the present invention, and your inventors have found that the effect is insensitive to structured material diameter. However, the material needs to be stiff enough to hold shape during application of the sound field.

The placement of structured material in the resonator chamber adds complexity to the sound field. For example, in the case of a cylindrical chamber, the simple linear series of nodes and antinodes along the cylindrical axis of the chamber is superimposed by a complex node structure in the shape of the structured material itself. Every part of the structure acts as an acoustic velocity node, and therefore, as a place where particles can be levitated and stored while the sound field is active. See FIG. 1, wherein discrete structures are put into a velocity antinode region (green) and the result is the addition of many small velocity nodes (blue regions above and below the structures).

Figure 5:
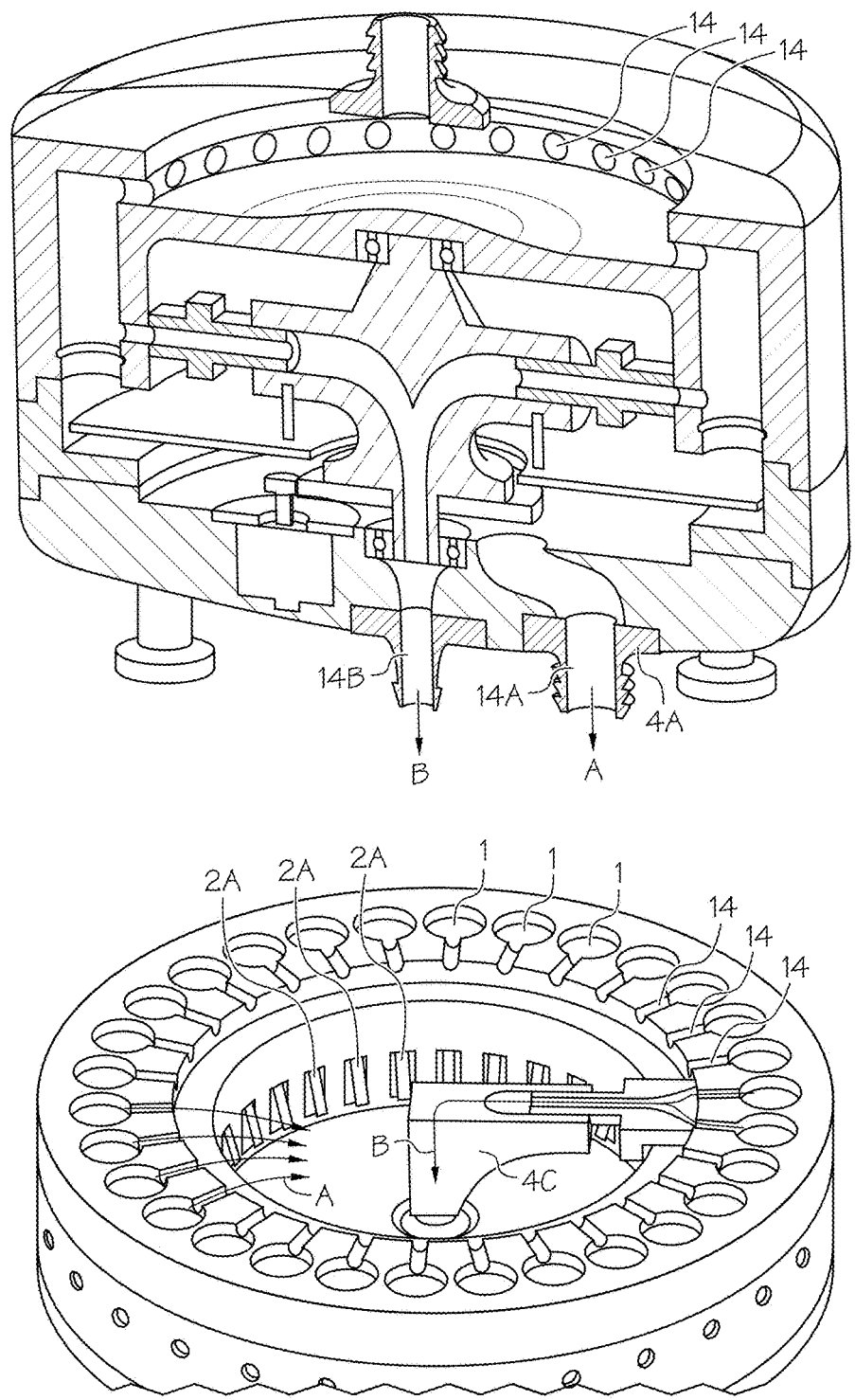
FIG. 5 is a center-cut view of a 30-resonator embodiment of the present invention, further described in Example 2.

Air flow through the resonator 1 may be adjusted, depending on whether the resonator is capturing or releasing particulate. The flow may be more significant if the resonator is capturing the particulate (with sound field applied), and pass over the filter at a slower rate if the particulate is being released (without sound field). Thus, as shown in FIGS. 5 and 12, the major air flow A may be drawn through the resonator 1 by a fan or pump 4A, while the minor air flow B (of concentrated sample) may be pulled by an external device that is receiving the concentrated flow (and sampling the same, as herein described) at that device's own rate(s). Alternatively, a separate external fan may be used to draw the minor flow. In systems having multiple resonators, one fan may be used to draw the major flow A through all resonators. The major flow may be from about 0.001 liters per minute (LPM) to 100,000 LPM; in some embodiments the major flow is between 1 and 60 LPM; in certain embodiments it is 8 LPM. The minor flow B may range from 0.001% to 50% of the major flow; in some embodiments the minor flow of concentrated aerosol is 0.5 LPM. Because the major flow is not itself dislodging the particulate from the fluid, the present invention has reduced overall power consumption over the prior art.

As shown in FIGS. 2 and 12, the top and/or bottom of the resonator housing 11 includes means to accommodate or affix one or more sound sources 2 for applying and removing a sound field within the structure-filled acoustic resonators 1. Such accommodation means may include apertures and o-rings, sized and shaped to accommodate the sound source; alternatively the sound source may be removably or permanently affixed to the interior of the housing 11. The sound pressure level and the frequency of the applied sound field are selected to trap a desired particulate or aerosol within the resonator; by removing or altering the sound field, trapped particulate can be released from the structured material and expelled from the resonator Any commercial off-the-shelf (COTS) piezoelectric ultrasonic sound sources may be used as the sound source 2 of the present invention, including those commonly used in motor vehicle "back-up sensors". Other sound sources may be used including, for example, electrodynamic sound sources such as loud speakers or compression drivers. In some embodiments, as shown in FIGS. 2 and 11, the ultrasonic sound source 2 is inserted into the bottom of the resonator housing 1, which is sized to receive the sound source either with or without an o-ring or similar sealing structure. The top of the ultrasonic sound source 2 may then act as the bottom of the resonator 1. The peak sound pressure level inside the resonator is about 150 dB re 20 microPascals. However, the effect works over a range of about 120 dB up to 190 dB peak sound pressure level.

When the sound field within the structure-filled acoustic resonator 1, produced by the sound source 2, is activated and air is passed through the resonator, the resonator functions as a 'virtual filter', whereby particulate may be temporarily accumulated therein. When the sound field is deactivated, nearly all particulate is released from its acoustic confinement, and with the fluid that continues to pass through the resonator (typically at a lower LPM), exits the resonator at the outlet port 14 or 14B as a concentrated surge of particulate. The sound field may be controlled by a switch 2A or other electronic or mechanical means.

With a single resonator system, the system expels either particulate-free fluid or particulate-concentrated fluid, depending on whether the sound field is activated or deactivated. In some embodiments of the present invention the sound field and air flow through the resonator 1 are controlled mechanically by means of a rotating outlet 5. As shown in FIG. 12, the mechanical control may further direct the air flow when the sound field is activated to the environment through a first port 14A, and direct the air-flow to the second outlet port 14B when the sound field is deactivated.

Figure 4:
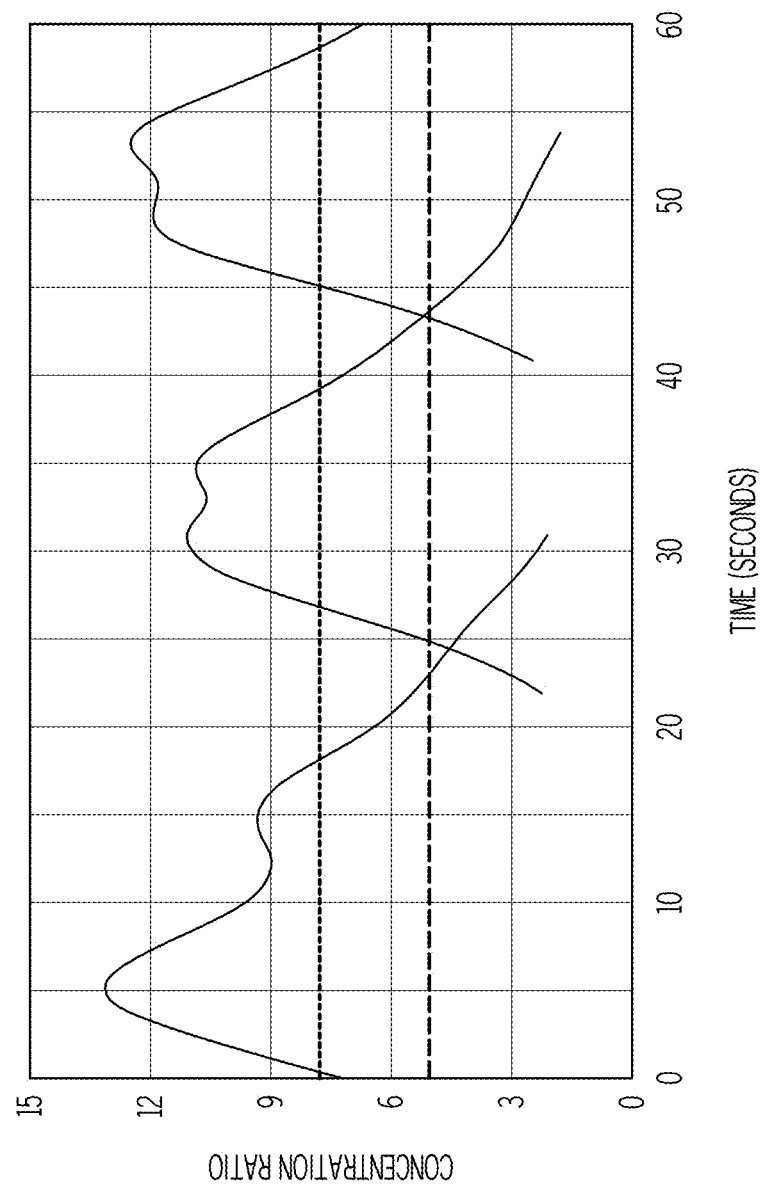
FIG. 4 shows concentration output from three aerosol surges (concentrated air streams from an acoustic resonator of the system of the present invention), overlaid to demonstrate how a continuous-flow output can be achieved using three resonators.

As evidenced in FIG. 4, in some embodiments of the present invention a continuous stream of concentrated particulate may be produced when multiple acoustic resonators 1 are operated in sequence by mechanical control mechanisms, such that the system cycles the functionality of its resonators (collecting or releasing particulate) in sequence to achieve a near-continuous concentrated particulate stream at the outlet. For example, the multiple resonators may be cycled similar to the functioning of a multi-cylinder internal combustion engine in which valves open and close sequentially as controlled by a cam shaft. In multiple-resonator embodiments, the resonators may be provided in parallel structure, or about a circumference as shown in FIG. 5. As shown in FIG. 4, three transient concentration surges may be produced sequentially to produce average (upper dotted line) and minimum (lower dashed line) concentration ratios of 8-to-1 and 5-to-1 respectively. An embodiment of a thirty resonator system is shown in FIG. 5; FIG. 11 shows an embodiment of a six resonator system.

The thirty-resonator embodiment shown in FIG. 5 provides a system wherein twenty-eight of the resonators are activated and air is pulled through those resonators by a common fan that expels air to the environment (flow path A); an extraction nozzle 4C rotates about the central axis in order to extract the concentrated aerosol from the remaining pair of resonators, and deliver it to an outlet 14B at the bottom-center to provide a near-continuous concentrated sample. In this embodiment, the rotating extraction arm 4C also depresses a switch 2A that deactivates the sound field in the remaining pair of resonators. Once the extraction arm has passed the resonators and proceeds on to the next two resonators in the sequence, the switch 2A is no longer depressed and the sound field is once again activated in the first pair of resonators until the arm completes another rotation.

Figure 13:
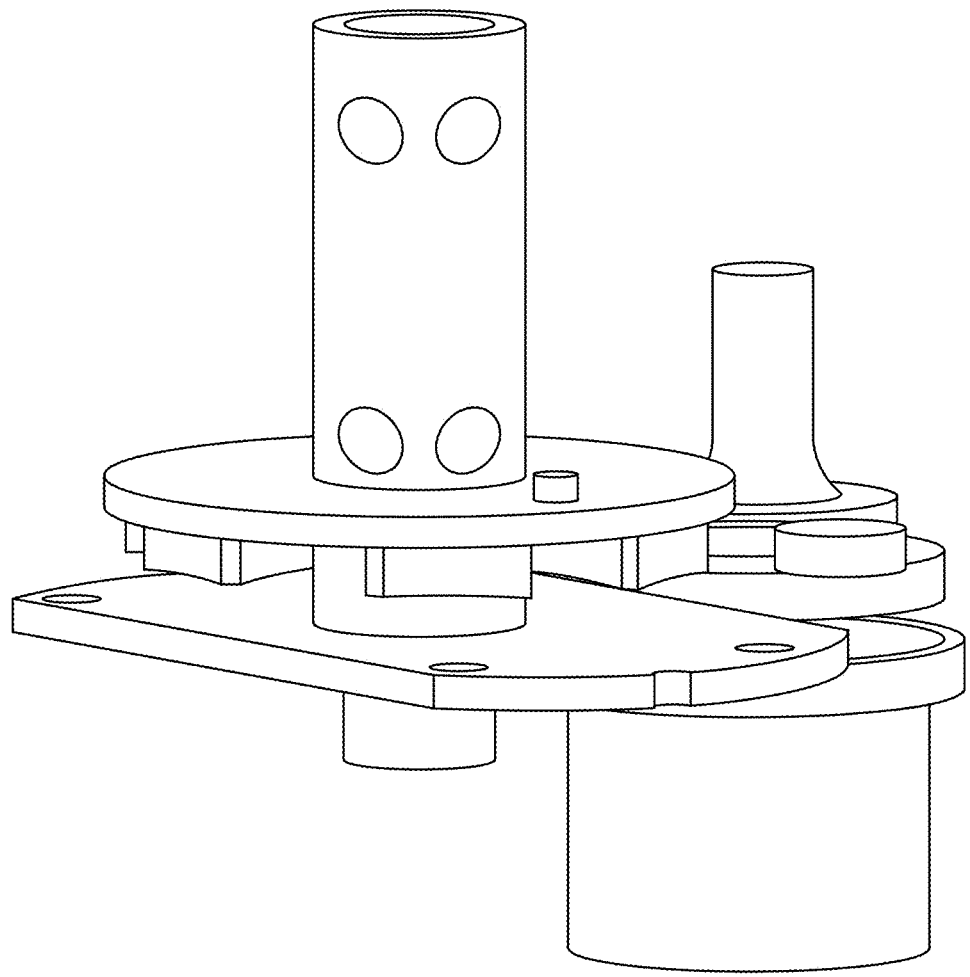
FIG. 13 shows the inner brass tube of the valving system for the embodiment of the present invention as shown in FIG. 11.

In a similar six-resonator embodiment shown in FIGS. 11 and 13, a rotating valving mechanism 4D is provided to sequentially capture exhaust from each of the six resonators. In this embodiment, the valving mechanism may include a rotating arm 4C (as depicted in FIG. 5) or may be designed and configured as a brass tube, as shown in FIG. 13. As shown in FIGS. 5 and 11, the valving mechanism passes in front of the resonator outlets sequentially; when the arm or tube is in front of an outlet, the individual resonator's sound field is deactivated and the concentrated aerosol is sucked out through the hollow arm or tube 14B. The rotation of the valving mechanism 4D may be controlled by an electric motor 6.

Figure 9A:
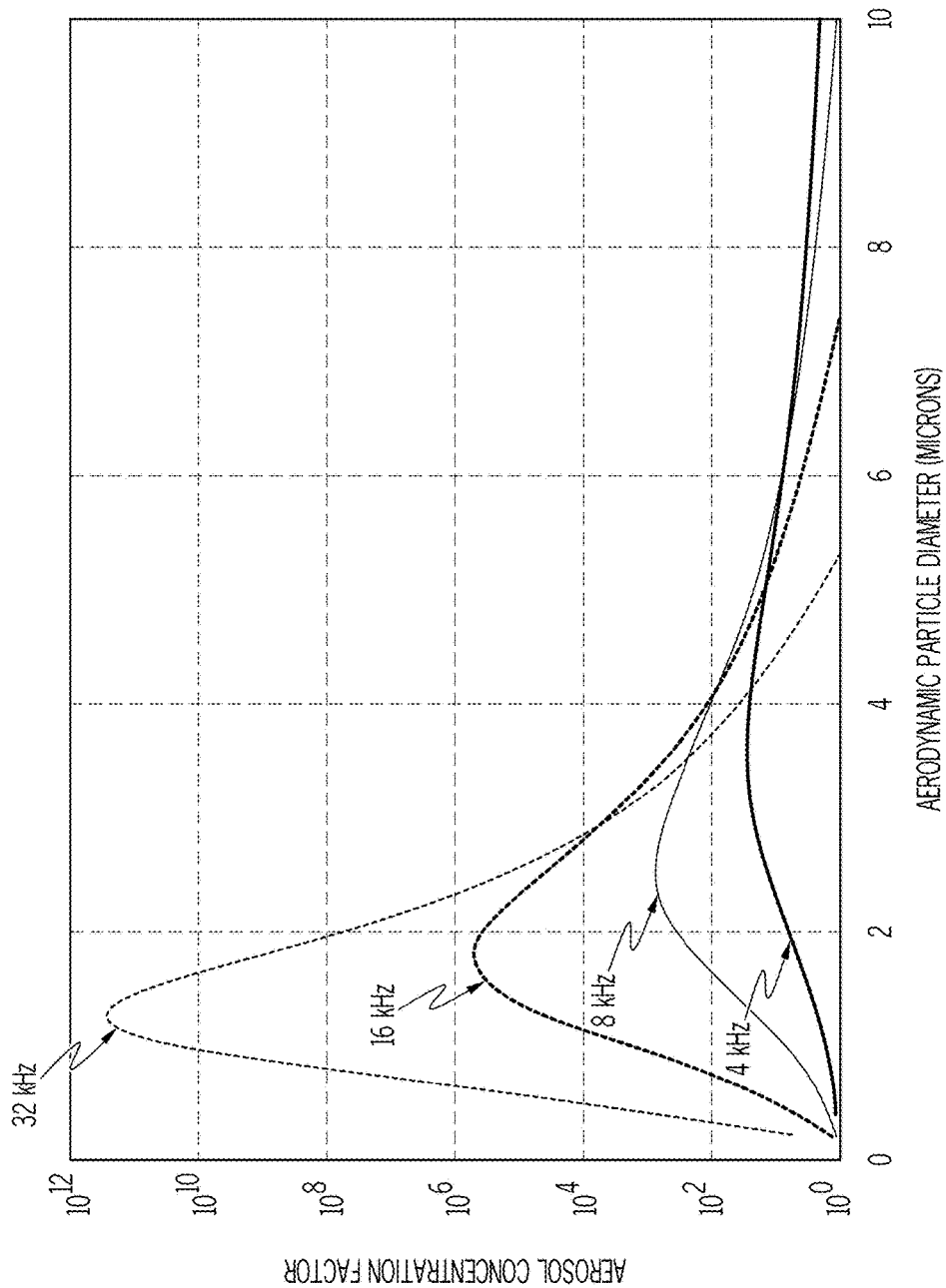
FIG. 9A shows a theoretical increase in aerosol concentration at the acoustic node by means of the system of the parent invention, based upon frequency of the sound applied to the acoustic resonator, and the size of the particles.
Figure 9B:
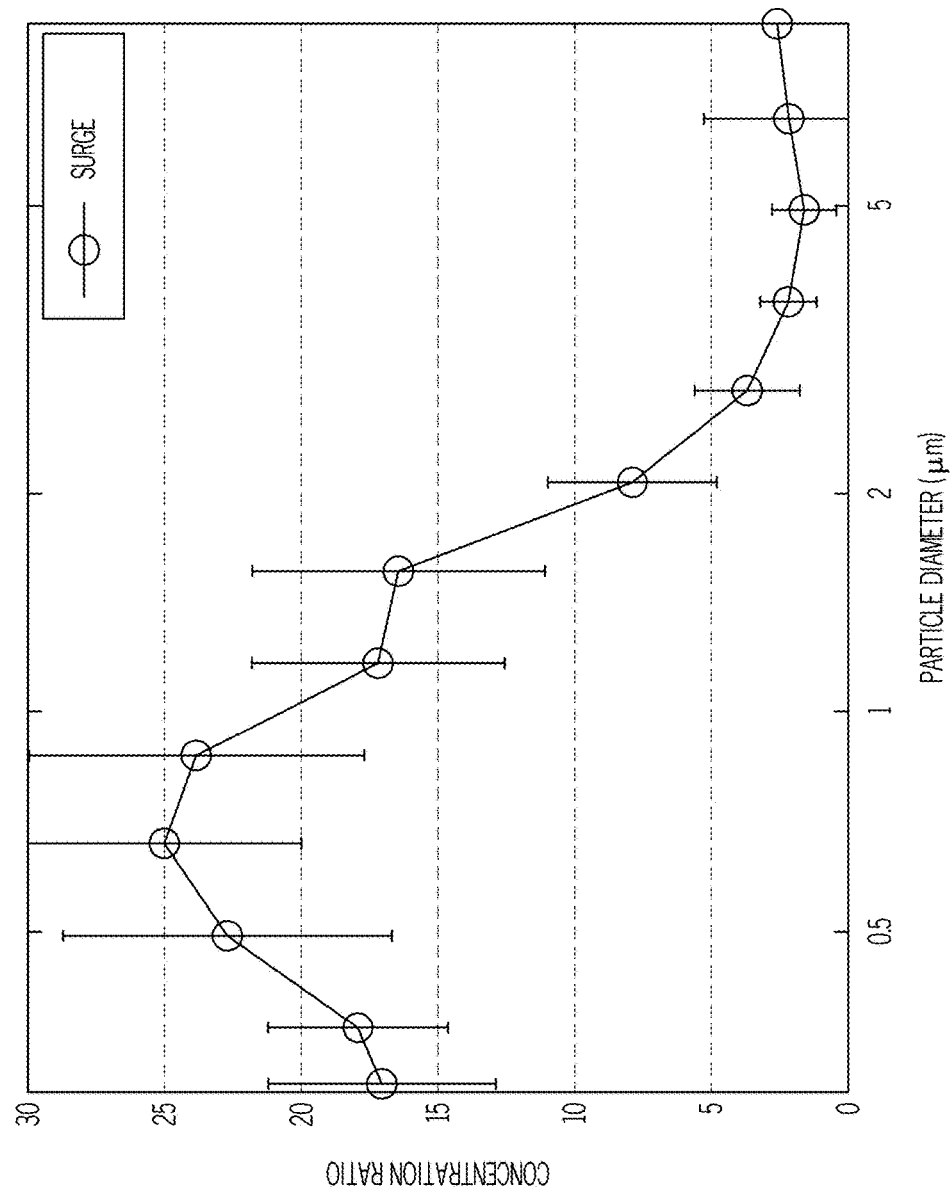
FIG. 9B shows adjustment to the concentration ratios based upon mean particle diameters.
Figure 9C:
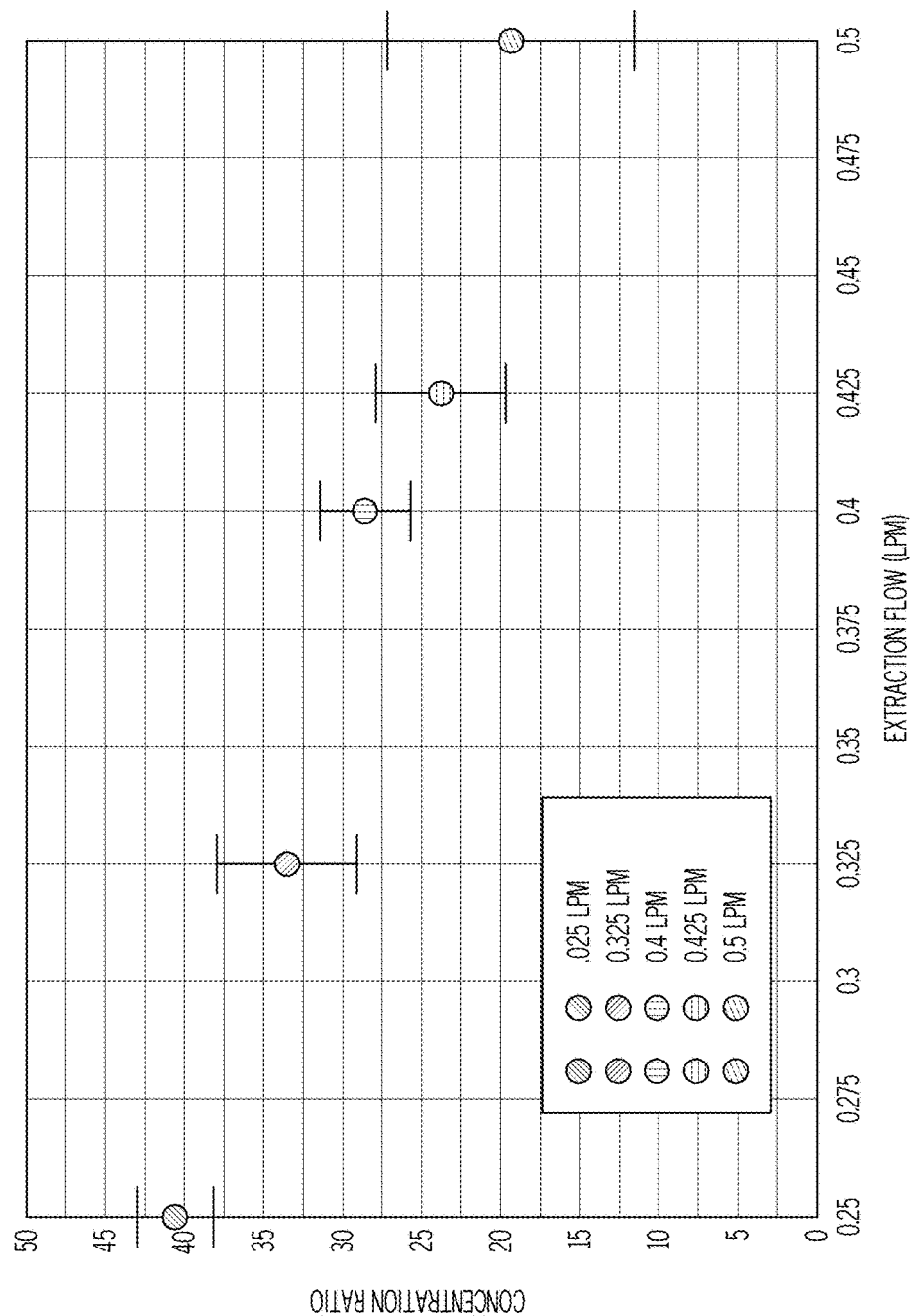
FIG. 9C shows concentration ratios changing with the rate of extraction flow.

The concentration factor can be adjusted by process control parameters including inlet flow rate, outlet flow rate, sound pressure level, sound activation time, frequency of sound, particle size, and other parameters. For example, as shown in FIG. 9A, theoretical modeling calculations reveal that the use of a lower frequency (e.g., 4 kHz) tends to concentrate larger particles more readily, and the use of a higher frequency (e.g., 32 kHz) tends to successfully concentrate smaller particles. FIG. 9B shows experimental data revealing similar trends, with the data generated by testing at 24 kHz, with a smaller particle size (0.6 microns) at peak concentration than the theoretical modeling (estimated at about 1.5 microns at peak concentration), demonstrating in part that the system of the present invention is more effective than the prior art at trapping, and delivering in a concentrated stream, smaller sized particles. As shown in FIG. 9C, the concentration ratio decreases with increasing extraction flow rate (minor flow rate). The testing in FIG. 9C was conducted after 1.25 LPM major flow, with a 60-second major flow time period. Sound pressure of the system of the present invention can be modified by changing the drive voltage to the ultrasonic transducers or other sound sources, which lowers or raises the sound pressure level from the sound source in the resonator.

Figure 10:
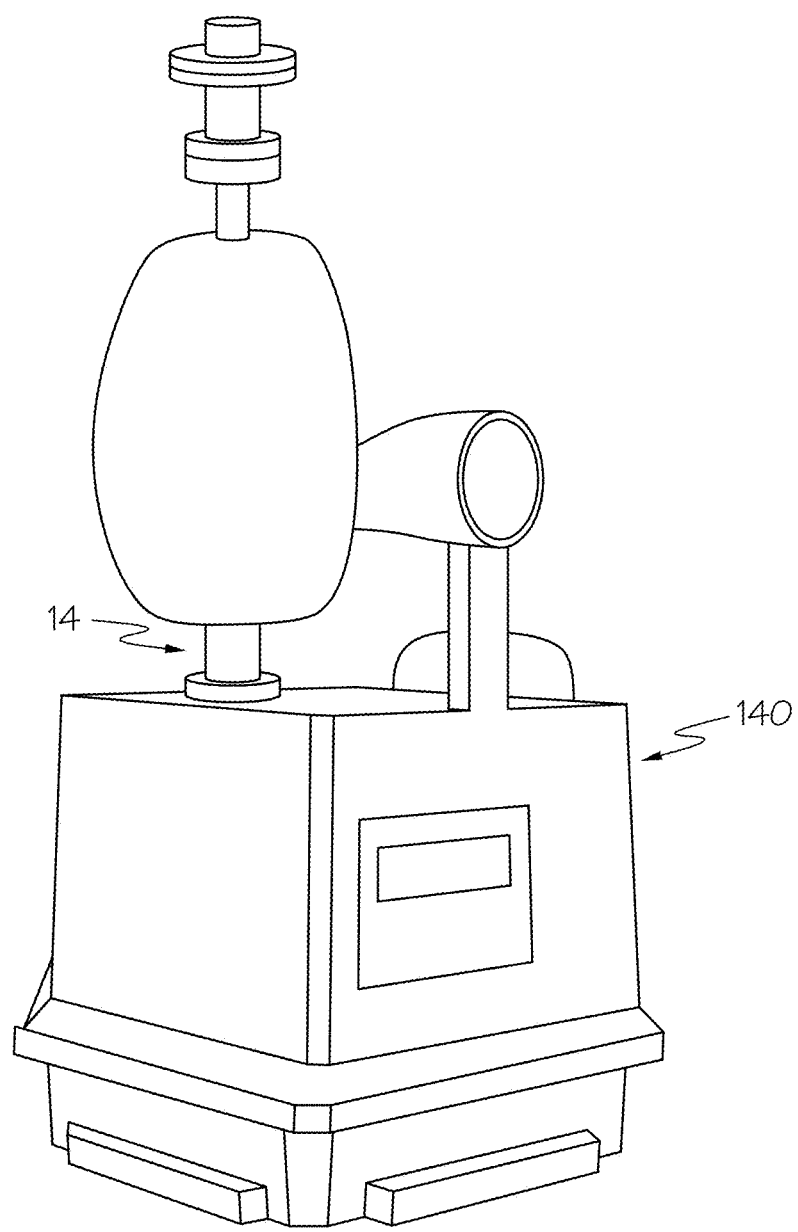
FIG. 10 depicts another embodiment of the system of the present invention.

The concentrated particulate flow from systems and methods of the present invention may be used in many applications such as material processing, aerosol sensing and detection, and similar and other methods of testing or using concentrated particulate fluids. A particularly beneficial application is attaching the system of the present invention, at the output port 14, to the inlet of aerosol detectors such as chemical-biological agent detectors, in order to increase the sensitivity of these devices and improve their ability to detect particulate of interest. For example, output port 14 of the acoustic concentrator of the present invention may be attached on the inlet port of a fluorescence aerosol detector 140 in order to increase the received fluorescence signal, as shown in FIG. 10. Suitable fluorescence aerosol detectors include the Tactical Biological Detector (TACBIO), the Rapid Agent Aerosol Detector (RAAD), and the Bio-Agent Sensor and Trigger (BAST).

Furthermore, the system of the present invention may be used in liquid applications, to remove and concentrate particles entrained in the liquid. For example, the system may be used to detect minute amounts of contaminants in drinking water to assure purity or attempt to detect intentional or accidental contamination of a water supply. Likewise, the system may be used to remove and concentrate cells (e.g., cancer cells) or other particulates from blood. Notably, the fibrous material must be denser and stiffer than the liquid.

The method of the present invention to concentrate particulate within an air sample using an aerosol/particulate concentrator device such as the device hereinabove described, includes drawing in a fluid sample into a structure-filled acoustic resonator and applying a sound field within the structure-filled resonator. The sound pressure level and frequency of the applied sound field are selected to trap a desired particulate or aerosol, as hereinabove described for the system of the present invention. The method also includes expelling fluid from the resonator. When the sound field is deactivated from the resonator, the method continues with releasing the trapped sample of particulate/aerosol in a concentrated fluid stream; activation and deactivation of the sound field may be electronically or mechanically controlled.

The method of the present invention may further include the use of additional structure-filled acoustic resonators, wherein the process is cycled through each resonator in a sequence to achieve a near continuous-flow of concentrated aerosol or particulate. Furthermore, the fluid released may be sampled for the concentrated particulate by means of a sensor selected from the group consisting of: chemical, biological, radionuclide, and explosives sensors.

As hereinabove described, adjustments to the sound pressure level may achieve varying levels of concentration of particulate, and adjustment of the frequency of the sound filed may achieve preferential concentration of different sizes or types of particulate/aerosols. In some embodiments, the applied frequency of the sound field is above 16 kHz, and the peak sound pressure level of the sound field in the resonator is above 140 dB.

Applications of the inventions as hereinabove described are demonstrated in the following examples:

Example #1

Figure 3:
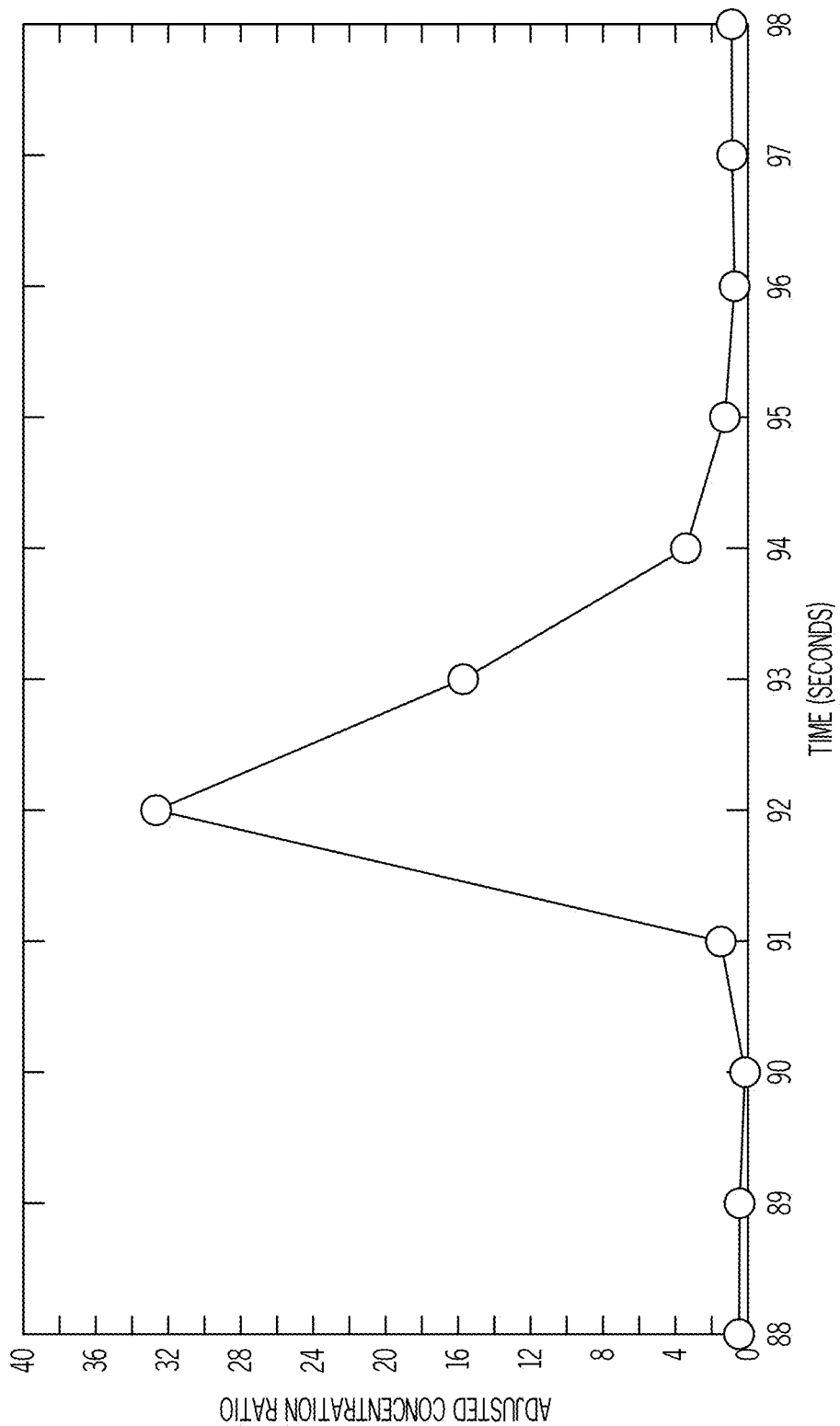
FIG. 3 shows transient concentration measurements acquired with the ultrasonic resonator of the embodiment shown in FIG. 2, as further described in Example 1.

A single-resonator ultrasonic concentrator was fabricated and tested. The device included a cylindrical resonator cavity with an ultrasonic transducer, and having inlet and outlet ports, as shown in FIG. 2. Tests were conducted with a 3.1 micron test particle entrained in air, where air was drawn through the resonator for 90 seconds with the sound field activated, and then the sound field was deactivated and air continued to flow at 0.25 LPM. As shown in FIG. 3, t 92 seconds, the stored aerosol was released in a surge producing a 34-to-1 aerosol concentration, and at about 95 seconds the output returned to the ambient 1-to-1 concentration (no concentration).

Example #2

Figure 6:
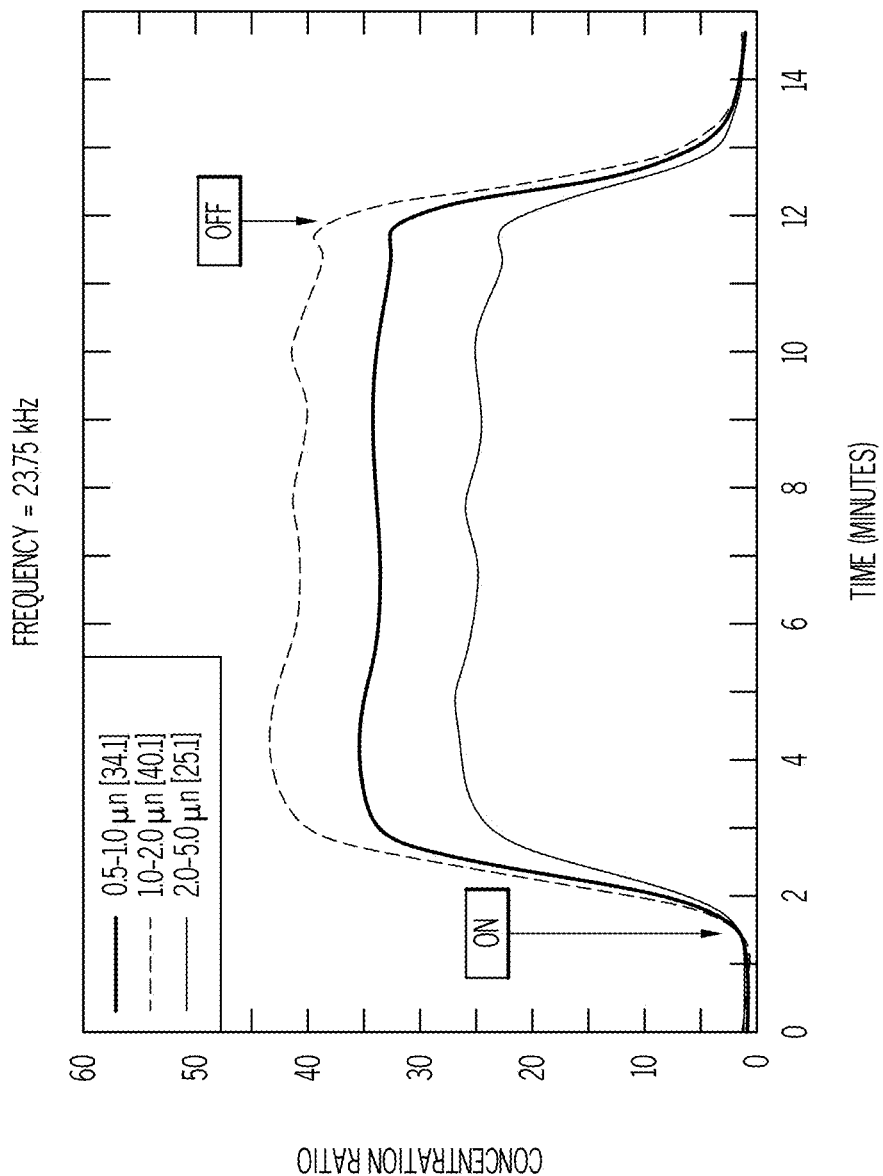
FIG. 6 shows results from testing of the embodiment of the present invention shown in FIG. 5, demonstrating a 40:1 concentration in the 1 to 2 micron size range.
Figure 7:
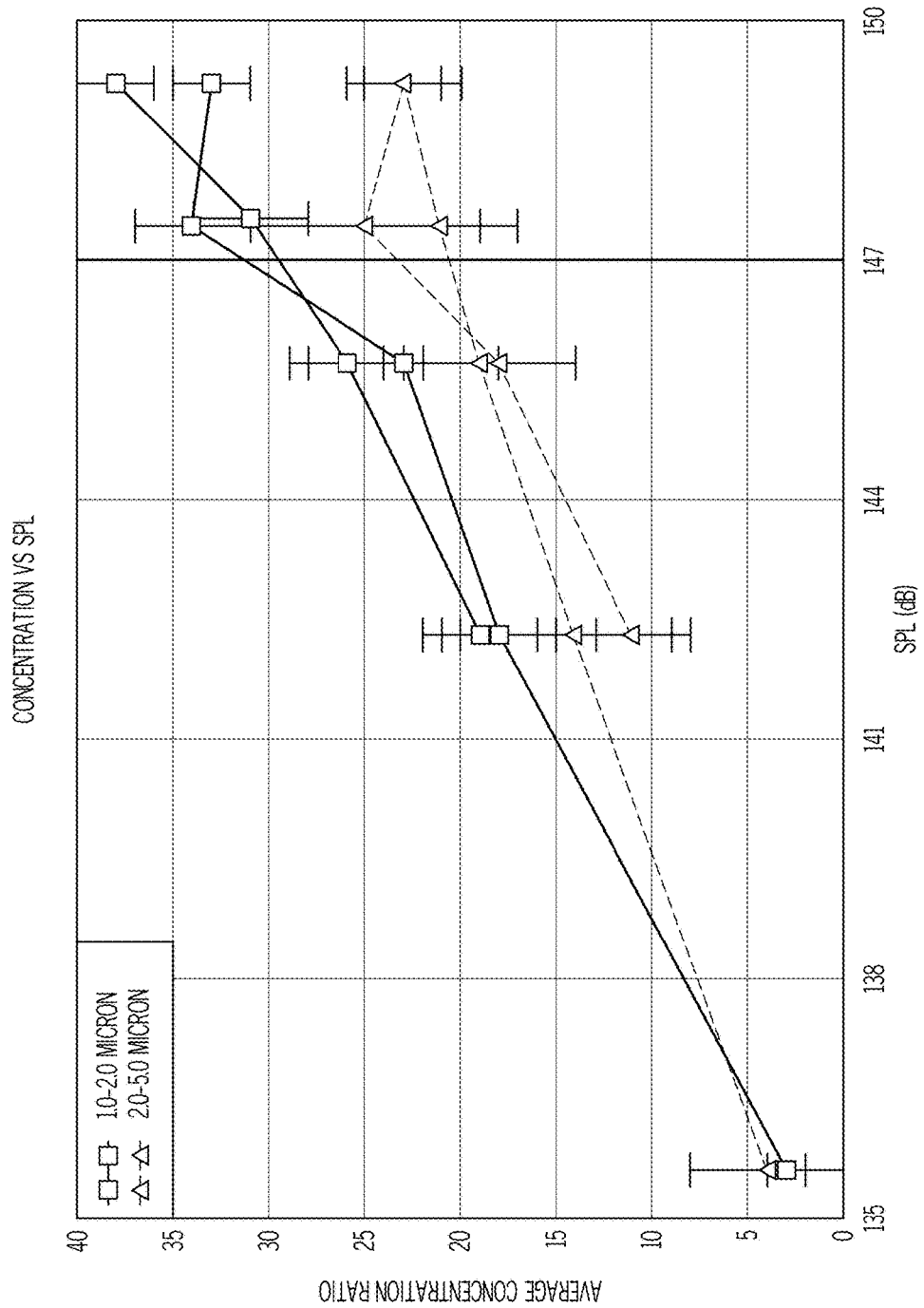
FIG. 7 shows results from testing of the embodiment of the present invention shown in FIG. 5, demonstrating adjustment of the concentration ratio based upon sound decibels.
Figure 8:
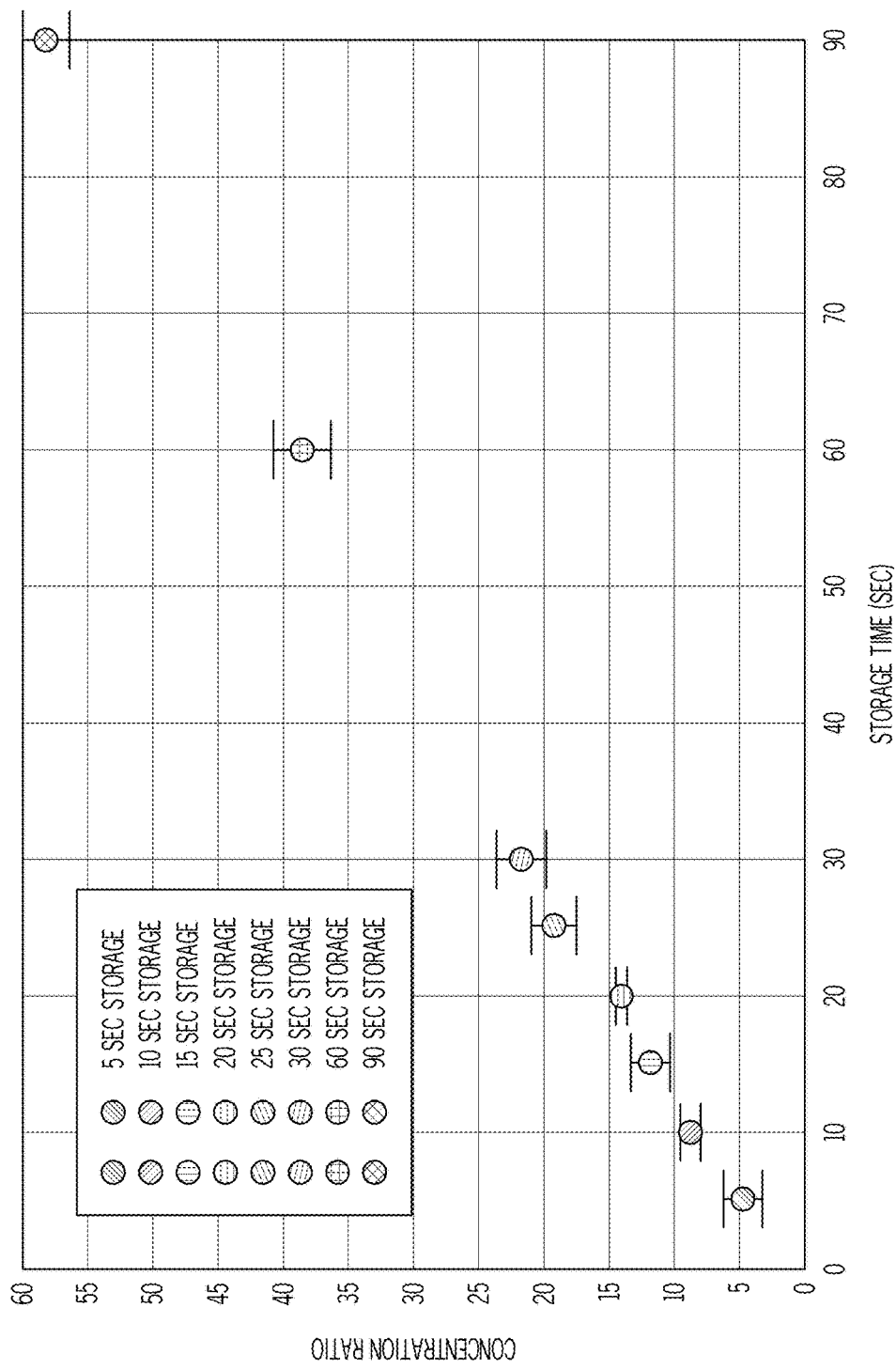
FIG. 8 shows results from testing of the embodiment of the present invention shown in FIG. 5, demonstrating an increase in particle concentration by increasing the amount of time that the sound field is activated before releasing a surge of concentrated particulate.

Data from the 30-resonator concentrator hereinabove described, and depicted in FIG. 5, is shown in FIG. 6, showing a concentration of 1 to 2 micron aerosols (the blue line) at a ratio of about 40-to-1. Smaller and larger particles are concentrated slightly less as shown by the red and black lines, respectively. Alteration of the applied frequency of sound, resonator geometry, and structured materials can be made to achieve a preferential concentration of a desired particle size. As shown in FIG. 7, the concentration ratio may be increased or decreased by adjusting the dive voltage applied to the ultrasonic transducer, and therefore the sound pressure level. As shown in FIG. 8, the particulate storage time may be adjusted to increase or decrease the level of concentration.

What is claimed is:

1. A particulate concentrator device comprising:
   a. a plurality of acoustic resonators, each resonator comprising an inlet port and one or more outlet ports, and being filled with structured material;
   b. one or more fans coupled with the plurality of resonators for drawing an air sample having particulates from an environment through the inlet port into the acoustic resonator, and for expelling air from the acoustic resonator through one or more of the outlet ports, resulting in a continuous airflow traversing the structured material of each acoustic resonator;
   c. a Piezoelectric ultrasonic sound source coupled with the plurality of resonators to apply a sound field in each of the resonators, wherein the sound source is further coupled with a plurality of switches, wherein each switch is associated with one or more of the resonators, and the position of the switch controls whether the resonator receives the applied sound field or the applied sound field is removed from the resonator; and
   d. an extraction nozzle movable among at least some of the resonator outlet ports to extract airflow of concentrated particulates from the resonator;
   wherein when the extraction nozzle is coupled with one of the resonators, the extraction nozzle deactivates the switch controlling the applied sound field for that resonator such that the applied sound field is removed from that resonator.

2. The device of claim 1, further comprising a plurality of sensors to receive the expelled air, wherein said sensors are selected from the group consisting of; chemical, biological, radionuclide, and explosives sensors.

3. The device of claim 1 further comprising a housing having
   a. a first housing outlet to receive airflow from the resonators engaged with the extraction nozzle, wherein the extraction nozzle rotates within the housing and delivers the airflow to the first housing outlet, and
   b. a second housing outlet to receive airflow from the other resonators.

4. The device of claim 3, wherein the extraction nozzle simultaneously extracts airflow of concentrated particulates from at least two resonators.

5. The device of claim 1, wherein the applied sound field has a sound pressure of between 120 dB and 190 dB.

6. The device of claim 1, further comprising a sensor selected from the group consisting of: chemical, biological, radionuclide, and explosives sensors.

7. The device of claim 1, wherein the applied sound field has a frequency set to achieve preferential concentration of a certain size or type of particulates.

8. The device of claim 1, wherein the applied sound field has a frequency of between 1 kHz and 32 kHz.

* * * * *

UNITED STATES PATENT AND TRADEMARK OFFICE
CERTIFICATE OF CORRECTION

PATENT NO. : 9,766,168 B2
APPLICATION NO. : 14/521156
DATED : September 19, 2017
INVENTOR(S) : Meegan et al.

It is certified that error appears in the above-identified patent and that said Letters Patent is hereby corrected as shown below:

In the Specification

Column 1, Line 7-8, "system and method for capturing particulates entrained in gaseous (e.g., aerosol) or liquid fluids, and delivering a" should read --system and method for capturing particulates (e.g., aerosol) entrained in gaseous or liquid fluids, and delivering a--.

Column 4, Line 26-27, "occurs at chamber lengths given by Length=1/2×N×(frequency of applied sound)/(speed of sound) where N=1,2,3," should read --occurs at chamber lengths given by Length=1/2×N×(speed of sound)/(frequency of applied sound) where N=1,2,3,--.

Column 6, Line 23, "expelled from resonator" should read --expelled from resonator.--.

Column 9, Line 19, "may be increased or decreased by adjusting the dive voltage" should read --may be increased or decreased by adjusting the drive voltage--.

Signed and Sealed this
Twenty-seventh Day of March, 2018

Andrei Iancu
*Director of the United States Patent and Trademark Office*